(12) United States Patent
Beck et al.

(10) Patent No.: US 9,977,011 B2
(45) Date of Patent: May 22, 2018

(54) PORTABLE SAMPLING DEVICE AND METHOD FOR SAMPLING DRUG SUBSTANCES FROM EXHALED BREATH

(75) Inventors: Olof Beck, Saltsjöö-Boo (SE); Bo Hammarlund, Sollentuna (SE)

(73) Assignee: Sensa Bues AB, Sollentuna (SE)

(*) Notice: Subject to any disclaimer, the term of this patent is extended or adjusted under 35 U.S.C. 154(b) by 1059 days.

(21) Appl. No.: 14/003,915

(22) PCT Filed: Mar. 9, 2012
(Under 37 CFR 1.47)

(86) PCT No.: PCT/EP2012/054180
§ 371 (c)(1),
(2), (4) Date: Feb. 18, 2014

(87) PCT Pub. No.: WO2012/120140
PCT Pub. Date: Sep. 13, 2012

(65) Prior Publication Data
US 2014/0366609 A1 Dec. 18, 2014

Related U.S. Application Data

(60) Provisional application No. 61/450,993, filed on Mar. 9, 2011.

(30) Foreign Application Priority Data

Mar. 9, 2011 (EP) .................................. 11157564

(51) Int. Cl.
*G01N 33/497* (2006.01)
*A61B 5/08* (2006.01)
(Continued)

(52) U.S. Cl.
CPC ............ *G01N 33/497* (2013.01); *A61B 5/082* (2013.01); *A61B 5/091* (2013.01); *A61B 5/097* (2013.01);
(Continued)

(58) Field of Classification Search
CPC .................................................... G01N 33/497
See application file for complete search history.

(56) References Cited

U.S. PATENT DOCUMENTS 3,316,904 A * 5/1967 Wall .................. A41D 13/1146
128/205.29
4,292,978 A 10/1981 Guth
(Continued)

FOREIGN PATENT DOCUMENTS

DE 19718924 10/1998
DE 10137161 A1 2/2003
(Continued)

OTHER PUBLICATIONS

Office Action dated Apr. 22, 2015, in connection with related Russian application No. 20139129331, filed Nov. 21, 2013.
(Continued)

*Primary Examiner* — Lisa Caputo
*Assistant Examiner* — Alex Devito
(74) *Attorney, Agent, or Firm* — Downs Rachlin Martin PLLC

(57) ABSTRACT

A portable drug sampling device for handheldly collecting a sample from exhaled breath of a subject for further sensor based analysis. The device comprising: a housing (406) comprising at least one inlet (407) and at least one outlet (408) for the exhaled breath to exit through, and a sampling membrane (302) arranged in the housing. A tubular element (40) having a mouthpiece section (401) for the subject to exhale into, and a saliva trap section comprising baffles (103) to create a non-straight gas flow path for letting aerosols pass through the tubular element. The sampling membrane (302) is arranged to collect the aerosols from the exhaled breath. The portable drug testing device further comprises a volume collecting element (208).

31 Claims, 5 Drawing Sheets

(51) Int. Cl.

| | | |
|---|---|---|
| *A61B 5/091* | (2006.01) | |
| *A61B 5/097* | (2006.01) | |
| *A61B 5/00* | (2006.01) | |
| *B29C 65/46* | (2006.01) | |
| *B29C 65/66* | (2006.01) | |
| *B29K 23/00* | (2006.01) | |
| *B29K 33/04* | (2006.01) | |
| *B29K 105/00* | (2006.01) | |

(52) U.S. Cl.
CPC ............ *A61B 5/4845* (2013.01); *B29C 65/46* (2013.01); *B29C 65/665* (2013.01); *B29K 2023/10* (2013.01); *B29K 2033/04* (2013.01); *B29K 2105/256* (2013.01); *B29K 2105/258* (2013.01); *G01N 2033/4975* (2013.01)

(56) References Cited

U.S. PATENT DOCUMENTS

| | | |
|---|---|---|
| 4,327,741 A | 5/1982 | Watson et al. |
| 4,809,810 A | 3/1989 | Elfman |
| 4,900,514 A | 2/1990 | Fuller |
| 5,042,501 A | 8/1991 | Kenny et al. |
| 5,195,527 A | 3/1993 | Hicks |
| 5,369,977 A | 12/1994 | Rhodes et al. |
| 5,465,728 A | 11/1995 | Phillips |
| 5,467,776 A | 11/1995 | Hamilton |
| 5,478,377 A | 12/1995 | Scavnicky et al. |
| 5,518,002 A | 5/1996 | Wolf |
| 5,721,102 A | 2/1998 | Vo-Dinh |
| 5,834,626 A | 11/1998 | De Castro |
| 6,097,480 A | 8/2000 | Kaplan |
| 6,209,541 B1 | 4/2001 | Wallace |
| 6,623,997 B2 | 9/2003 | Farquharson et al. |
| 7,285,246 B1* | 10/2007 | Martin .................. A61B 5/097 422/408 |
| 7,450,227 B2 | 11/2008 | Dwight et al. |
| 8,368,883 B2 | 2/2013 | Palmskog et al. |
| 8,705,029 B2 | 4/2014 | Palmskog et al. |
| 2002/0007249 A1* | 1/2002 | Cranley ............... G01N 33/497 702/24 |
| 2002/0095078 A1 | 7/2002 | Mannheimer et al. |
| 2002/0177232 A1 | 11/2002 | Melker et al. |
| 2003/0028120 A1 | 2/2003 | Mault et al. |
| 2004/0045889 A1* | 3/2004 | Harkonen ............. B01D 45/06 210/304 |
| 2004/0236244 A1 | 11/2004 | Allen |
| 2005/0048660 A1 | 3/2005 | Bearer |
| 2005/0051719 A1 | 3/2005 | Miller et al. |
| 2005/0065446 A1* | 3/2005 | Talton .................. G01N 1/2214 600/529 |
| 2005/0137491 A1* | 6/2005 | Paz ........................ A61B 5/097 600/543 |
| 2005/0233459 A1 | 10/2005 | Melker et al. |
| 2006/0021302 A1* | 2/2006 | Bernard ............. B01D 46/0028 55/282 |
| 2006/0038990 A1 | 2/2006 | Habib et al. |
| 2006/0078467 A1 | 4/2006 | Stock |
| 2006/0084182 A1 | 4/2006 | Farquharson et al. |
| 2006/0119853 A1 | 6/2006 | Baumberg et al. |
| 2006/0153740 A1 | 7/2006 | Sultan et al. |
| 2006/0160134 A1 | 7/2006 | Melker |
| 2006/0266353 A1 | 11/2006 | Yamada et al. |
| 2007/0023627 A1 | 2/2007 | Finch et al. |
| 2007/0156211 A1 | 7/2007 | Ferren et al. |
| 2007/0185405 A1 | 8/2007 | Altobelli |
| 2007/0224128 A1 | 9/2007 | Dennis et al. |
| 2007/0252077 A1 | 11/2007 | Shoji |
| 2007/0258894 A1 | 11/2007 | Melker et al. |
| 2008/0183388 A1 | 7/2008 | Goodrich |
| 2010/0036272 A1 | 2/2010 | Mace et al. |
| 2010/0083838 A1 | 4/2010 | Togashi |
| 2010/0264042 A1 | 10/2010 | Varney et al. |
| 2011/0053173 A1 | 3/2011 | Hood |
| 2011/0098590 A1* | 4/2011 | Garbutt ................ A61B 5/0059 600/532 |
| 2012/0212735 A1 | 8/2012 | Palmskog et al. |
| 2012/0302907 A1 | 11/2012 | Palmskog et al. |
| 2013/0066223 A1 | 3/2013 | Beck et al. |
| 2013/0128260 A1 | 5/2013 | Palmskog et al. |
| 2014/0065602 A1 | 3/2014 | Milton |
| 2015/0033824 A1 | 2/2015 | Hammarlund et al. |
| 2016/0034809 A1 | 2/2016 | Trenholm |

FOREIGN PATENT DOCUMENTS

| | | |
|---|---|---|
| EP | 0997733 | 5/2000 |
| EP | 2518499 | 10/2012 |
| JP | H04507204 | 12/1992 |
| JP | 07120462 | 5/1995 |
| JP | 08510948 | 11/1996 |
| JP | 2001-505660 A | 4/2001 |
| JP | 2004-301749 A | 10/2004 |
| JP | 2007-525670 A | 9/2007 |
| JP | 2008102048 | 1/2008 |
| JP | 2009-047593 A | 3/2009 |
| WO | 0184112 A1 | 11/2001 |
| WO | 3057521 | 7/2003 |
| WO | 2005098429 | 10/2005 |
| WO | 2009030957 A1 | 3/2009 |
| WO | 2009045163 | 4/2009 |
| WO | 2011029888 | 3/2011 |

OTHER PUBLICATIONS

Amendment and Response filed with RCE dated Oct. 28, 2015, in connection with U.S. Appl. No. 13/416,956, filed Mar. 9, 2012.
Office Action dated Dec. 17, 2015, in connection with U.S. Appl. No. 14/222,696, filed Mar. 24, 2014.
Amendment filed with RCE dated Dec. 21, 2015, in connection with U.S. Appl. No. 13/394,609, filed May 29, 2012.
Office Action dated Jan. 7, 2016, in connection with U.S. Appl. No. 14/427,229, filed Mar. 10, 2015.
Office Action dated Feb. 17, 2016 related to U.S. Appl. No. 13/394,609, filed May 29, 2012, Goran Palmskog.
Office Action dated Feb. 1, 2016 related to U.S. Appl. No. 13/416,956, filed Mar. 9, 2012, Olof Beck.
Response to Office Action dated May 14, 2015, in connection with related U.S. Appl. No. 13/394,609, filed May 29, 2012.
Final Office Action dated Jun. 19, 2015, in connection with related U.S. Appl. No. 13/394,609, filed May 29, 2012.
Response to Final Office Action dated Aug. 19, 2015, in connection with related U.S. Appl. No. 13/394,609, filed May 29, 2012.
Advisory Action dated Sep. 2, 2015, in connection with related U.S. Appl. No. 13/394,609, filed May 29, 2012.
Final Office Action dated Apr. 28, 2015, in connection with related U.S. Appl. No. 13/416,956, filed Mar. 9, 2012.
Response to Final Office Action dated Jun. 29, 2015, in connection with related U.S. Appl. No. 13/416,956, filed Mar. 9, 2012.
Advisory Action dated Jul. 24, 2015, in connection with related U.S. Appl. No. 13/416,956, filed Mar. 9, 2012.
Almstrand, Ann-Charlotte et al: "Airway monitoring by collection and mass spectrometric analysis of exhaled particles", Analytical Chemistry, American Chemical Society, vol. 81, No. 2, Jan. 15, 2009, pp. 662-668, XP007915715; ISSN: 0003-2700.
Beck, Olof et al., "Study on the sampling of methadone from exhaled breath", Journal of Analytical Toxicology, vol. 35, No. 5, Jun. 2011, pp. 257-263, XP55045425.
Beck, Olof et al., "Demonstration that methadone is being present in the exhaled breath aerosol fraction", Aug. 3, 2011, Journal of Pharmaceutical and Biomedical Analysis, pp. 1024-1028, ISSN: 0731-7085.
Bernd Sagmuller et al, Application of SERS Spectroscopy to the identification of (3,4-methylenedioxy) Amphetamine in Forensic Samples Utilizing Matrix Stabilized Silver Halides, Oct. 2001, pp. 2066-2071, vol. 126, No. 11, The Analyst, The Royal Society of Chemistry 2001.

(56) References Cited

OTHER PUBLICATIONS

Buszewski Boguslaw et al., "Human exhaled air analytics: biomarkers of diseases," Biomedical Chromatography, Jun. 2007, pp. 553-566 & 588, vol. 21, No. 6.
EPO Communication re Personal Consultation with Examiner, dated Dec. 10, 2012, issued in connection with EP10751947.2. related.
EPO Communication, Article 94(3) dated Mar. 7, 2013, issued in connection with related EP10751947.2.
EPO Communication, Article 94(3) dated Oct. 23, 2012, issued in connection with related EP10751947.2.
European Search Report dated Jun. 8, 2011, in connection with related EP Application No. 11157565.
Extended European Search Report dated Apr. 11, 2012, in connection with related EP Application No. 12 15 8911.
Fabian, Patricia et al., "Influenza virus in human exhaled breath: an observational study", PLOS One 2008, vol. 3, No. 7, Jul. 16, 2008, p. e2691, XP7921865, ISSN: 1932-6203.
International Preliminary Report on Patentability dated Oct. 27, 2011, in connection with related PCT/EP2010/063265 filed Sep. 9, 2010.
International Search Report and Written Opinion dated Nov. 19, 2010, for related application PCT/EP2010/063266 filed Sep. 9, 2010, entitled "Drug Detection in Exhaled Breath," Palskog, G et al.
International Search Report dated Nov. 24, 2010, in connection with related PCT/EP2010/063265 filed Sep. 9, 2010.
International Search Report dated May 23, 2013, in connection with related PCT/EP2013/054789, filed Mar. 8, 2013.
International Search Report dated Oct. 4, 2013, in connection with related PCT/EP2013/068860, filed Sep. 11, 2013.
Marks, P, "Taking on the drugged and drunk drivers," New Scientist, Reed Business Information, Surrey, GB, vol. 188, No. 2528, Dec. 3, 2005, pp. 28-29.
Miekisch, W et al., "Assessment of propofol concentrations in human breath and blood by means of HS-SPME-GC-MS," Clinica Chimica Acta, Elsevier BV, Amsterdam, NL, Sep. 1, 2008, pp. 32-37, vol. 395, No. 1-2.
Mutlu G. M., et al., "Collection and analysis of exhaled breath condensate in Humans", American Journal of Respiratory and Critical Care Medicine, American Lung Association, NY, NY, vol. 164, 2001, pp. 731-737, XP003012811, ISSN: 1073-449X.
Sagmuller et al., Application of SERS spectroscopy to the identification of (3,4-methylenedioxy)amphetamine in forensic samples utilizing matrix stabilized silver halides, Analyst, Royal Society of Chemistry, GB, vol. 126, No. 11, Nov. 1, 2001, pp. 2066-2071.
Sanchez, C et al., "Determination of Nitroaromatic Compounds in Air Samples at Femtogram Level Using C18 Membrane Sampling and On-line Extraction with LC-MS," Analytical Chemistry, Sep. 1, 2003, pp. 4639-4645, vol. 75, No. 17.
Sulk et al., Surface-Enhanced Raman Scattering Detection of Amphetamine and methamphetamine by Modification with 2-Mercaptonicotinic Acid, Applied Spectroscopy, the Society for Applied Spectroscopy, Baltimore, US, vol. 53, No. 8, Jan. 1, 1999, pp. 954-959.
Written Opinion dated Apr. 11, 2012, in connection with related EP Application No. 12 15 8911.
Written Opinion dated Jun. 8, 2011, in connection with related EP Application No. 11157565.
Written Opinion dated May 23, 2013, in connection with related PCT/EP2013/054789, filed Mar. 8, 2013.
Office Action dated Oct. 21, 2013, in connection with related Japan Application No. Tokugan-2012-528364.
Office Action dated Nov. 14, 2014, in connection with related U.S. Appl. No. 13/394,609, filed May 29, 2012.
Office Action dated Aug. 2, 2013, in connection with related U.S. Appl. No. 13/739,607, filed Jan. 11, 2013.
Response to Office Action dated Dec. 2, 2013, in connection with related U.S. Appl. No. 13/739,607, filed Jan. 11, 2013.
Office Action dated Aug. 13, 2014, in connection with related U.S. Appl. No. 13/416,956, filed Mar. 9, 2012.
Response to Office Action dated Jan. 13, 2015, in connection with related U.S. Appl. No. 13/416,956, filed Mar. 9, 2012.
Written Opinion dated Jul. 3, 2014 in connection with related EP14164314.8, filed Sep. 9, 2010.
European Search Report dated Jul. 3, 2014 in connection with related EP14164314.8, filed Sep. 9, 2010.
Zwir-Ferenc, A., et al., Solid Phase Extraction Technique—Trends, Opportunities and Applications; Polish J. of Environ. Stud., vol. 15, No. 5 (2006); pp. 677-690.
International Search Report dated Apr. 2, 2012, issued in connection with related PCT/EP2012/054180, filed: Mar. 9, 2012.
Written Opinion dated Apr. 2, 2012, issued in connection with related PCT/EP2012/054180, filed: Mar. 9, 2012.
Beck, O, et al., "Method for determination of methadone in exhaled breath collected from subjects undergoing methadone maintenance treatment"; Journal of Chromatography, vol. 878, No. 24, Aug. 15, 2010, pp. 2255-2259; ISSN: 1570-0232.
Periago, J. F. et al.; "Design and evaluation of an exhaled breath sampler for biological monitoring of organic solvents," Journal of Applied Toxicology, vol. 12, No. 2, Apr. 1, 1992; pp. 91-96; ISSN: 0260-437X.
Beck, O., et al., "Amphetamines detected in exhaled breath from drug addicts: A new possible method for drugs-of abuse testing," Journal of Analytical Toxicology, vol. 34, No. 5, Jun. 1, 2010; ISSN: 0146-4760.
Amendment and Response to First Non-Final Office Action dated Oct. 11, 2016, in connection with U.S. Appl. No. 14/383,846, filed Sep. 8, 2014.
Office Action dated Jul. 11, 2016, in connection with U.S. Appl. No. 14/383,846, Hammarlund.
Final Office Action dated Aug. 26, 2016, in connection with U.S. Appl. No. 13/416,956, Olof Beck.
Final Office Action dated Aug. 18, 2016, in connection with U.S. Appl. No. 13/394,609, Palmskog et al.
Response to Office Action dated Jun. 1, 2016, in connection with U.S. Appl. No. 13/416,956, filed Mar. 9, 2012, Olof Beck.
Amendment and Response to First Non-Final Office Action dated Apr. 18, 2016, in connection with U.S. Appl. No. 14/222,696, Palmskog et al.
Amendment and Response to First Office Action after RCE dated May 17, 2016, in connection with U.S. Appl. No. 13,394,609, Palmskog et al.
Amendment and Response to First Office Action dated Apr. 6, 2016, in connection with U.S. Appl. No. 14/427,229, Beck.
Notice of Allowance dated Apr. 26, 2016, in connection with U.S. Appl. No. 14/427,229, Beck.
Final Office Action dated Jun. 15, 2016, in connection with U.S. Appl. No. 14/222,696, Palmskog, et al.

* cited by examiner

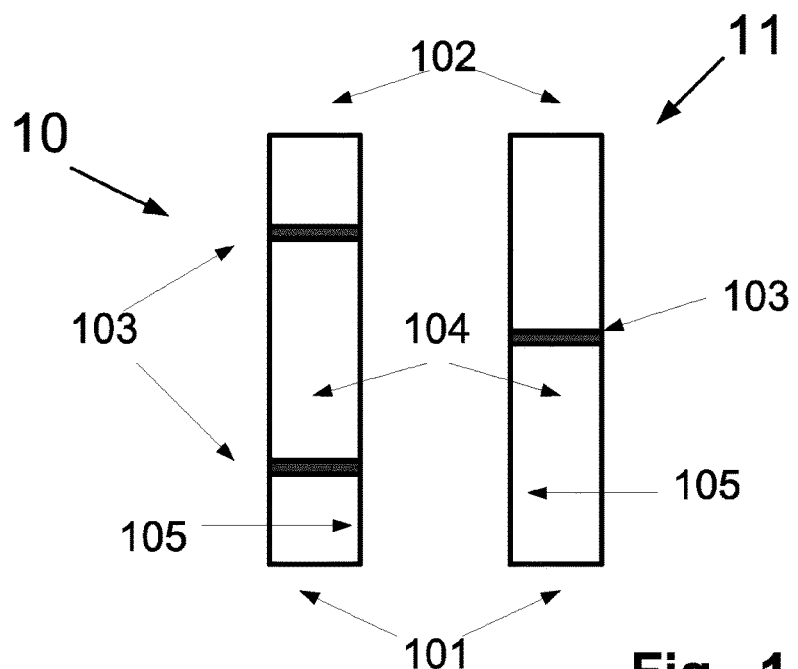
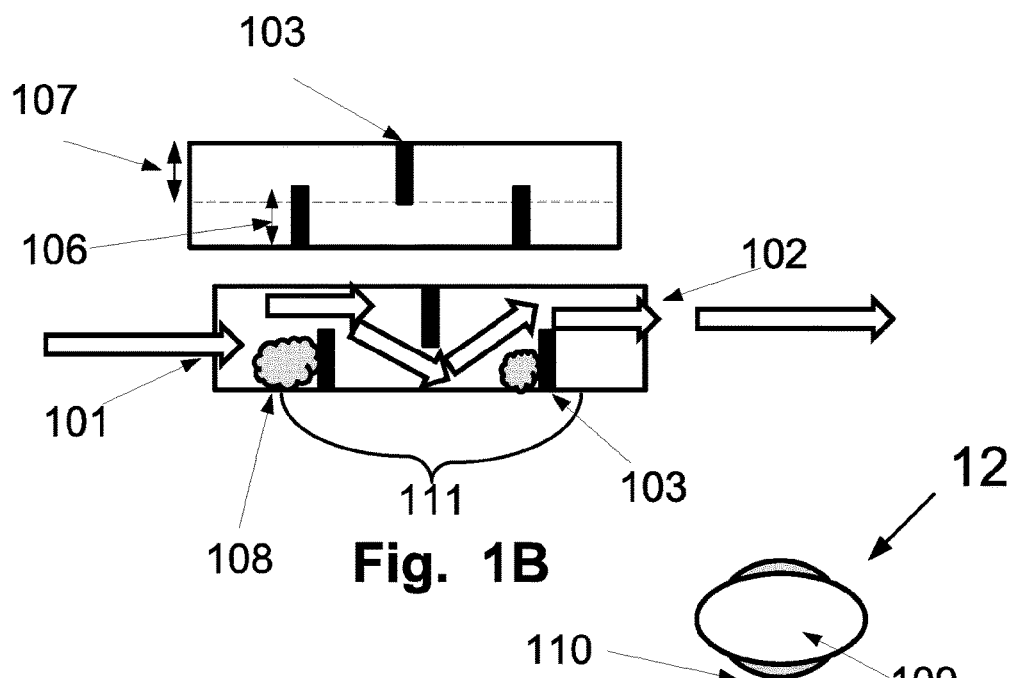
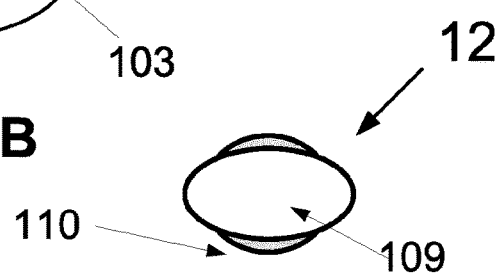

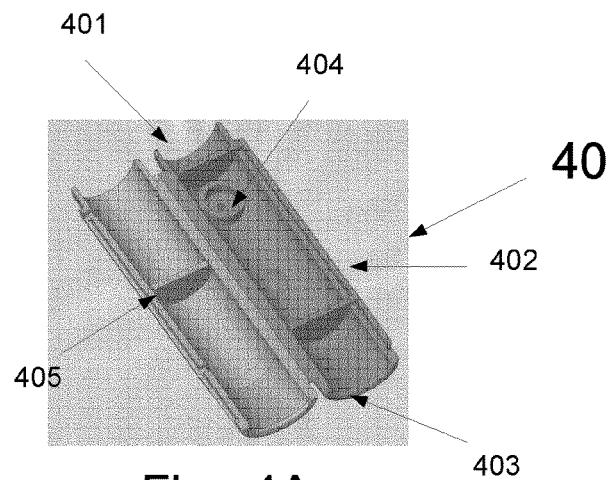
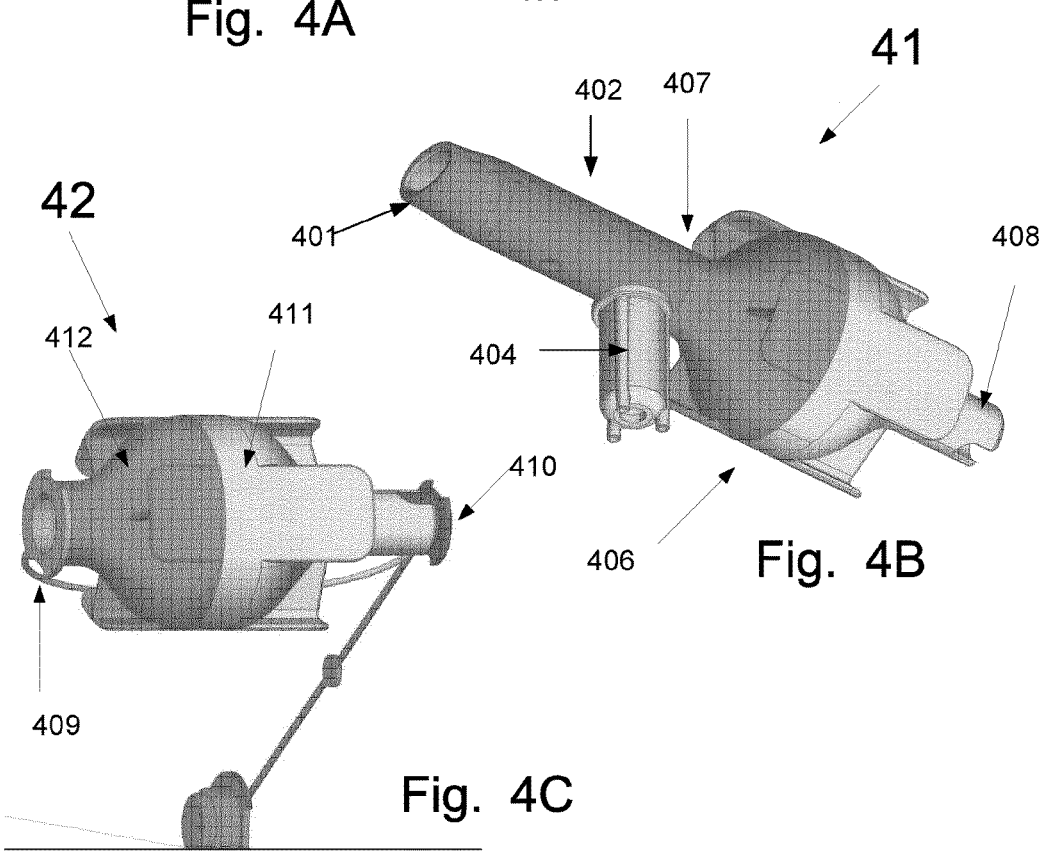

and a sampling membrane arranged in the housing.

PORTABLE SAMPLING DEVICE AND METHOD FOR SAMPLING DRUG SUBSTANCES FROM EXHALED BREATH

FIELD OF THE INVENTION

This invention pertains in general to the field of portable handheld devices, sampling systems and methods for collecting a sample from exhaled breath of a subject, and for detecting the presence (i.e. qualitative) or determining the quantitative amount of at least one illicit drug substance or compound in exhaled breath. More particularly the invention relates to such portable handheld devices.

BACKGROUND OF THE INVENTION

It is known that exhaled breath is commonly used in alcohol testing and today's technology makes it possible to perform on-site breath testing with legally defensible results using infrared spectroscopy.

Testing for other illicit drugs of abuse traditionally requires blood or urine samples. Alternatively specimens comprising hair, sweat or oral fluid could be used. Blood sampling is invasive and requires medically trained personnel, whereby test subject often have to be transported to a hospital for sampling. These procedures are time and effort consuming. With long lead times the test result will be too old. Urine sampling may also be considered intruding on personal integrity. Even other issues related to samples and specimens taken from a subject to be tested arise. For instance, blood samples, and especially urine samples are at risk of the subject exchanging the samples or using clean samples from another subject to avoid being discovered with traces of illicit drugs.

Thus, there is a need to provide a non-invasive, not-specimen based apparatus, system and/or method for detecting the presence (i.e. qualitative) or determining the quantitative amount of at least one drug substance in a subject. Particularly a device and method which should be easy to use with no or little training, especially a device and method for directly, at the site/on-site, screening a person for illicit drugs and obtaining results that could be approved by court.

Hence, an improved apparatus, system and/or method for at site/on site sampling of a subject for drug substances are desired. Such a device, system and/or method for sampling the subject for illicit drugs of abuse and/or medical drugs would be desired. The apparatus, system and/or method should be efficient, non-bulky, user friendly both for operators and the subject. It should further be not intruding and not invasive.

Another application would be to take samples from exhaled breath for sampling aerosols which may transport biomarkers. The samples could then be analyzed and detected biomarkers may be used for diagnosis of medical conditions of the tested subject. Measuring biomarkers in exhaled air would be non-invasive and enables repeated sampling which can be useful for early detection of disease as well as monitoring of disease progression and therapy response.

A known method for sampling biomarkers is Exhaled Breath Condensate (EBC) i.e. exhaled water vapor that is condensed by the means of low temperature. Both volatile and non-volatile compounds have been identified using EBC. The non-volatiles found in EBC are believed to originate from particles formed within the airways. The collection of exhaled breath condensate (EBC) is connected with a number of serious methodological difficulties such as dilution with water resulting in very low concentrations of the substances of interest, high contamination with substances originating from the oral cavity, high intraindividual coefficient of variation and a very inefficient way to sample, especially, non-volatiles compounds Hence, a method solving the short come of methods for easy monitoring of the airways that also allows frequent sampling would be advantageously. Particularly if the method may be performed risk free. Thus, there is a need to provide a non-invasive based apparatus, system and/or method for detecting the presence (i.e. qualitative) or determining the quantitative amount of at least one biomarker for medical diagnosis of a subject. Particularly, a device and method being easy to use with no or little training, especially a device and method to be used directly, at the site/on-site, for sampling and/or testing a subject for a medical diseases or illnesses would be advantageously. The device and method should have a sensitive for biomarkers high enough to obtain results of a standard that could be used for diagnosis of medical conditions.

Hence, an improved apparatus, system and/or method for at site/on site sampling of biomarkers from a subject is desired. The apparatus, system and/or method should be efficient, non-bulky, user friendly both for operators and the subject.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a system and a method, according to the appended patent claims.

According to one aspect of the invention, a portable drug substance sampling device is provided for collecting a sample from exhaled breath of a subject for further sensor based analysis. The device comprising a housing comprising at least one inlet and at least one outlet for the exhaled breath to exit through and a sampling membrane arranged in the housing.

The device further comprising a tubular element having a mouthpiece section for the subject to exhale into. The tubular element is a selective trap section in fluid communication with the mouthpiece and the inlet of the housing and the selective trap section is having a non-straight gas flow path for letting aerosols pass through said tubular element.

The sampling membrane is arranged to collect the aerosols from the exhaled breath. Further the device comprising a volume measure unit for determining that a pre-defined volume of the exhaled breath has passed through the sampling membrane.

The exhaled breath volume is not stored in a volume for analysis of the chemical contents of the entire breath volume. Rather, traces of the drug substance are attached to a sampling membrane. Analysis is not made online of the breath volume, but of the traces in the sampling membrane. The portable drug testing device may be sealed and sent further for the analysis, such as in a laboratory. Collection of the traces is made quickly, by exhaling a predetermined volume of breath through the sampling membrane. The obtain results when using the device are reliable and have a proven robustness. Using the invented drug testing device is far more convenient, quicker and cheaper than any previous breath sample collection methods.

Compounds exhaled in expired air may originate from blood by a mechanism of producing a gas phase in the alveoli. Alternatively, compounds may originate from other parts of the airways. Non-volatile compounds are transferred from the lungs carried by an aerosol. Here the non-volatile are drug substances or compounds and could be either medical drugs or legal or illegal narcotic substances or markers thereof. The drug substances are collected on-site using a portable system comprising a sampling membrane. The collected samples are to be sent to a laboratory for further analysis. Alternatively, compact on-site analysis equipment may be used to perform the analysis. The analysis is performed using a suitable analyzing method like spectroscopy or preferably mass-spectroscopy or Surface enhanced Raman spectroscopy (SERS). Other similar sensitive methods known to the skilled person may be used.

Since the portable drug testing device is small and designed to be easy to handle it may be used by any personnel anywhere on-site. Thus the drug testing device is adapted to be used instead of more intrusive tests, like tests based on the much common urine or blood samples.

The housing could be made of any material like, plastic, metal or glass as long as it is possibly to either clean or preferable be aseptic but could also be used sterile. The housing could alternatively or in addition be made of a disposable material. In this way the housing may, after being used for sampling and after the analysis of the collected compounds has been performed, be discarded.

The tubular section is used to improve the quality of the test by preventing big particles and/or aggregates and/or saliva to be collected by the sampling membrane. This may be done by having a selective trap section in the tubular section which has baffles to force the exhaled breath to pass a non-straight gas flow path.

In some embodiments of the invention, the tubular element is detachable from the housing or the tubular element is an integrated part of the housing.

In some embodiments of the invention, the volume measure unit is configured to measure a volume proportional to the pre-defined volume of the exhaled breath.

In some embodiments of the invention, a port is arranged downstream the mouthpiece and upstream the sampling membrane. The port is adapted to extract a defined portion of the exhaled breath into the volume measure unit.

In some embodiments of the invention, the volume measure unit comprising a gas volume collecting element, such as a bag, having a volume and wherein a port is arranged downstream the mouthpiece and upstream the sampling membrane and wherein the port is adapted to extract a defined portion of the exhaled breath into the volume measure unit.

This is an easy and effective way of determining when a pre-defined volume of exhaled breath has passed through the sampling membrane. The bag is blown up by utilizing the back pressure due to air flow resistance of the sampling membrane. The volume of the gas volume collecting element is proportional to the pre-defined volume of the exhaled breath.

In some embodiments of the invention, the volume collecting element is a non-elastic bag with a predetermined volume and/or size.

An elastic bag could be used but a non-elastic bag with a specific volume is easier to blow up and can only hold that specific volume.

In some embodiments of the invention, the sampling membrane is a filter membrane, preferably an electrostatic filter membrane.

In some embodiments of the invention, The filter membrane comprising at least one layer of non-woven filtration media with a specific weight in the range of 23 g/m3 to 500 g/m3, preferably in the range of 150 up to 300 g/m3, and even more preferably in the range of 200 up to 280 g/m3.

In some embodiments of the invention, the filter membrane comprising at least on further layer being a spun-bonded carrier with a scrim weight of 10 to 20 g/m3.

One important parameter of a sampling device that is fulfilled by using a filter membrane made of fibers is the low pressure drop. To be able to collect exhaled breath samples from most subjects the pressure drop through the system has to be as low as possible. The flow rate of a subject's exhalation depends on some parameters for example the subject's age, mental state (MR, Alzheimer's), medical condition (sepsis, Parkinson's) or other medications like benzodiazepines, opiates, neuroleptics, local anesthetics or intoxicants etc. Many people with a history of drug abuse have a very low flow rate.

In some embodiments of the invention, the filter membrane has a filter surface to be passed by exhaled gas of approximately 800 mm2 and a pressure drop of 36 Pa at 9.5 m/min media velocity.

In some embodiments of the invention, the filter membrane is made of a blend of acrylic fibers and polypropylene fibers.

The acrylic fibers have electrostatic properties while the polypropylene fibers will make the filter structure stronger, for example may the polypropylene fibers give the filter membrane enough support so that requires sizes and shapes can be punched out from the material.

In some embodiments of the invention, the housing may have at least two outlets.

Two outlet will help to prevent a subject to be tested from stopping the air from flowing out of the outlet and thereby preventing enough exhaled breath from passing through the sampling element.

In some embodiments of the invention, the tubular element further comprises an inlet, an outlet in connection with a lumen, at least two baffles, each having a height of at least a length of a radius of the lumen. The baffles are arranged on different sides of the lumen to deny an exhaled breath a straight path through the lumen of the conduit, thereby creating the selective trap section, which primarily the aerosols in the exhaled breath are permitted to pass though.

In some embodiments of the invention, each baffle may comprise orifices with a size that only permit the aerosols to pass through.

In some embodiments of the invention, the aerosols comprise non-volatile compounds of at least one drug substance in the exhaled breath. The drug substance is comprised in the list comprising Amphetamine, ecstasy, *Cannabis*, THC and cannabinoids, Opiates, heroin, morphine, 6-AM, Cocaine, Benzodiazepines, Propoxyphene, Methadone, Buprenorphine, Tramadol, LSD, Designer/Internet drugs, Kathinon, GHB, Meprobamat, Z-drugs, Tryptamines, or Anabolic steroids but are not limited to these since other illicit drugs (drugs of abuse) not included in the list may also be detectable due to similar interchanges with the human body as the above mentioned illicit drug substances.

According to another aspect of the invention, the portable drug testing device may be used for non-intrusive breath testing a subject for illicit drug substances, preferably as a substitute for testing the subject for the drug substance by sampling blood or urine.

The compositions of the exhaled particles are believed to reflect the airway's mucus layer and/or respiratory tract lining fluid, which probably reflects the blood content of the drug. The drug substances or compounds are believed by the inventors to most likely to come from the central part of the airway system. The non-volatile drug substances or compounds are carried by liquid droplets (aerosol) that are formed during normal breathing, for example, by the turbulent airflow causing the airway-lining fluid to nebulize. The aerosols are possible to collect as exhaled breath condensates. The theory comes from Anesthetic studies that have showed that Anesthetic potency correlates with lipid solubility. Holds true across species and implies when a specific hydrophobic region is occupied the more soluble the anesthetic agent is in blood the faster the drug goes into the body.

According to yet another aspect of the invention, a system is provided for detecting the presence and/or determining the quantitative amount of at least one drug compound in said exhaled breath. The system comprising a portable drug testing device and a sensor unit for analyzing a sample collected from exhaled breath of a subject by means of said device.

The mass-spectroscopy or SERS are the preferred analyzing methods, since this technology has a very high selectivity and sensibility of bioanalysis especially with regards to trace analytes in biological samples. The preferable interface for the mass spectroscopy is liquid chromatography.

The sampling membrane may be emptied from collected particles and analyzed by dissolving the collected particles from the exhaled breath in a solvent. The solvent could than be analyzed by the sensor unit. Another method could be to evaporate the content of the sampling membrane onto a SERS surface.

In a further aspect of the invention, a process to manufacture the portable drug testing device is provided, the process comprising: heating a first part of a plastic housing, thereby enlarging the first part's circumference. The process further comprises seating a sampling membrane in close proximity to an opening, not being an outlet or an inlet, of the first part. Moreover, the process comprises employing the heat from the first part for melting the sampling membrane at an edge. The process further includes utilizing the melted edge for fastening the sampling membrane to the housing. Further, the process includes sliding a fraction of a second part of the housing, having a temperature lower than the first part, inside of the first part. The first part when cooling down will shrink and a tight fit is obtained around the fraction of the second part and at the same time the housing will encapsulating the sampling membrane.

In a further aspect of the invention, a system for detecting the presence or determining the quantitative amount of at least one drug compound in the exhaled breath is provided. The system comprising a device for drug testing, and a sensor unit for analyzing a sample collected from exhaled breath of a subject by means of said device.

The system may be used to determining the presence of a drug substance in the exhaled breath either quantitative and/or qualitative.

In yet another aspect of the invention, a method of screening a person for drugs is provided. The method comprising, collecting a sample from exhaled breath of a subject, such as by using the herein disclosed device for drug sampling, and sensor based analysis of the sample. The method comprising, the subject exhaling into the device. Collecting aerosols from the exhaled breath in a sampling membrane of the device. Measuring a pre-defined fraction of the exhaled breath volume for determining a specific total volume of the exhaled breath passing through the sampling membrane. When the specific total volume is determined as having passed through the sampling membrane terminating the exhalation and sealing the device off. The method further comprises extracting content from the sampling membrane. Employing a sensor unit for detecting traces of the drugs in the content, and analyzing a presence of the drugs based on a result obtained from the sensor unit.

Further embodiments of the invention are defined in the dependent claims, wherein features for the second and subsequent aspects of the invention are as for the first aspect mutatis mutandis.

Alternative and/or additional, embodiments of the invention, provides for a portable sampling device for collecting aerosols comprising biomarkers from exhaled breath of a subject for further sensor based analysis. By sampling biomarkers from exhaled breath the device may help providing vital information for early detection and/or diagnosis of diseases or illnesses as well as monitoring of disease progression and/or therapy response.

Devices, systems and methods for sampling non-volatile biomarkers are in accordance with the devices, systems and methods for sampling of drug substances and/or compounds herein described.

Some known non-volatile biomarker that may be transported by aerosols in exhaled breath is comprised in the list comprising lipids, peptides, nucleotides, prostanoids, proteins, DNA or RNA.

These biomarkers may be used for diagnosis of diseases or illnesses, such as cancer (such as lung cancer), asthma, inflammation, infection (such as tuberculosis) and/or oxidative stress or other medical conditions.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1A-C are schematic illustrations showing an embodiment of a tubular element with a mouthpiece section, and a selective trap section designed to mainly permit aerosols from exhaled breath from a subject to pass through;

FIG. 4A is depicting a tubular section;

FIGS. 4B and C are depicting a portable sampling device at different stages of use;

DESCRIPTION OF EMBODIMENTS

Figure 2:
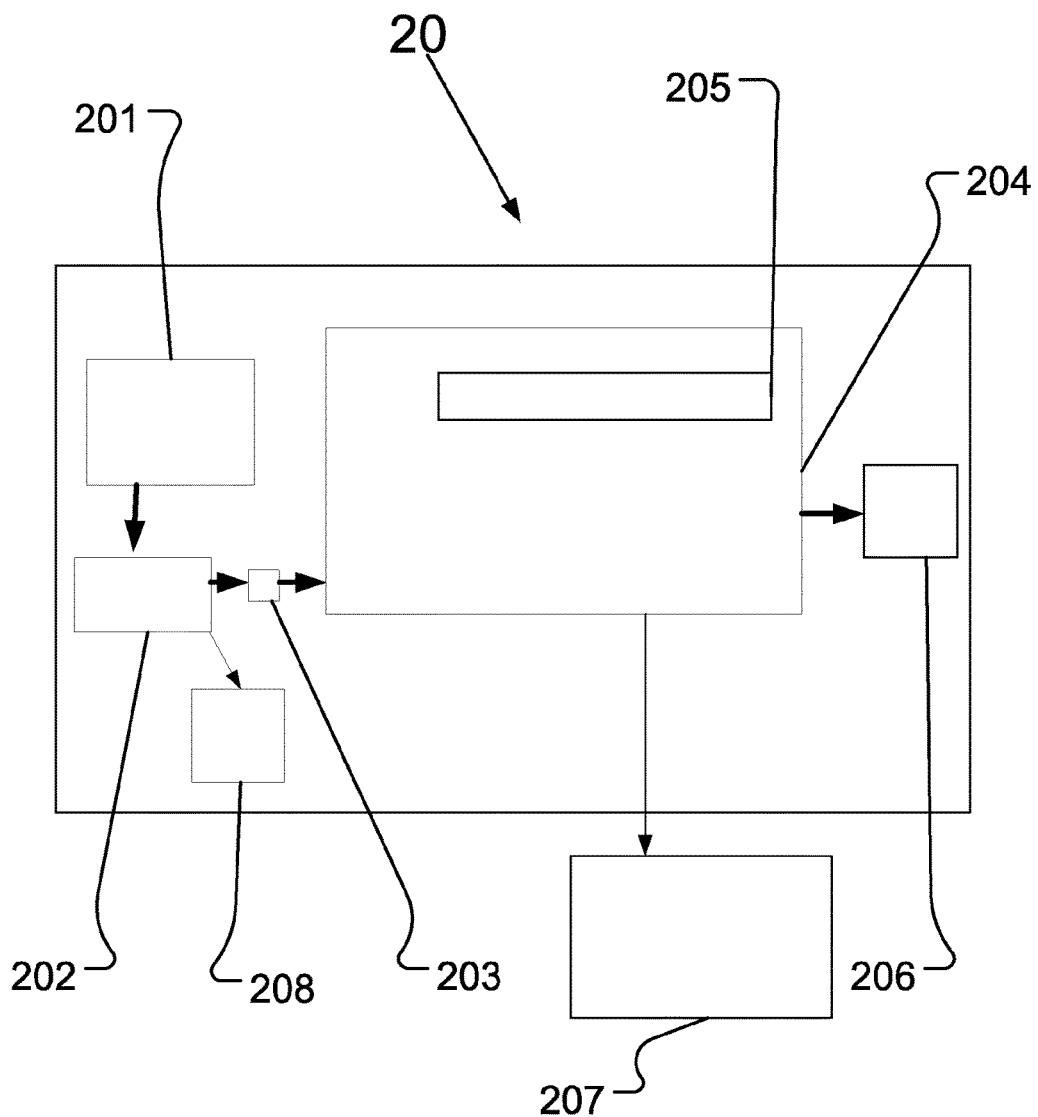
FIG. 2 is a schematic illustration illustrating an embodiment of a portable device configured to collect a sample from exhaled breath of a subject.

Specific embodiments of the invention will now be described with reference to the accompanying drawings.

This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

In an embodiment of the invention according to FIG. 1A-C a tubular element with a mouthpiece section and a selective trap section is depicted. The selective trap section of the tubular element is designed to permit primarily aerosols to pass through. Hence denying saliva and/or mucus and/or larger particles and/or aggregated to enter the housing and thereby avoiding the sampling membrane to be clogged.

The tubular element is a conduit with a coaxial lumen having transversal baffles. The cross-section of the lumen could have any shape but is preferably circular or oval. In FIG. 1A two complementary cross-section views 10, 11 along the length of a tubular element with a mouthpiece section are shown. The shape of the two parts are close to two half-pipes, wherein both parts comprising open ends 101, 102 which will form an inlet, being a mouthpiece section, and an outlet, when put together. The section between the inlet 101 and outlet 102 is a selective trap section 111 (see FIG. 1B). In FIG. 1A, part 10 comprises two transversal baffles 103 and part 11 one. Hence the total number of baffles 103 seated in the lumen 104 in the illustrated embodiment of the tubular element is three. In reality any suitable number of baffles needed to obtain the needed effect could be seated in the lumen of the tubular element. The section of the tubular element with the baffles 103 forms the selective trap section 111

The transversal baffles 103 may be perpendicular to the inner wall 105 of the lumen 104 (as depicted in FIG. 1A). Alternatively and/or additionally, in some embodiments the transversal baffles 103 may have any suitable angle relative the inner wall 105 of the lumen 104.

In FIG. 1B a cross-section of the tubular element is depicted from a different view, showing the height of the transversal baffles and the path the exhaled breath must travel from the inlet 101 to the outlet 102. In the upper cross-section view the height 106 of the baffles 103 are shown related to the radius 107 of the lumen. The baffles 103 protrude into the lumen 104 at least a distance being the same as the radius 107. Preferably the height 106 of the baffles 103 should be taller than the length of the radius 107 of the lumen 104. The baffles 103 are in FIG. 2B depicted as perpendicular to the inner wall 105 of the lumen 104. In reality each baffle 103 could have any suitable angle relative the inner wall 105 of the lumen 104 as long as they extend into the lumen the same distance as the radius 107 or longer.

The baffles 103 in the selective trap section 111 should be spaced to optimizing passing of aerosols and at the same time minimizing the amount of saliva and/or mucus and/or particles and/or aggregates 108 permitted through the tubular element to the outlet 102. Alternatively and/or additionally, in some embodiments the spacing is depending on the height and/or the angle of the baffles 103.

Further in FIG. 1B, the arrows in the lower cross-section show the non-straight travel of exhaled breath and of the aerosols through selective trap section 111 of the tubular element. The aerosols will easily travel from the inlet 101 to the outlet 102 while the heavier or larger in size particles or aggregates 108 that may clog a sampling membrane will be denied by the baffles 103. The selective trap section 111 of tubular element may therefore act as a pre-filter.

Alternatively and/or additionally, in some embodiments of the invention the baffles 103 include orifices sized to mainly permit aerosols to pass through the orifices.

In FIG. 1C the mouthpiece section 12 is depict. The inlet 109 could have any shape but one that has shown to be particularly suitable and comfortable is an oval shape. 110 depict the contours of the tubular section previously described in FIGS. 4 A and B.

In FIG. 2 is a schematic illustration showing an embodiment of a portable system configured to collect a sample from exhaled breath of a subject. Sampling system 20 is configured to collect a sample from exhaled breath of a subject 201. The subject will exhale through a mouthpiece and a tubular element 202 being in flow communication with a housing 204 via at least one inlet 203. The mouthpiece and tubular element 202 may be of same size or type as a conventional used for alcohol-test. Preferably the mouthpiece and tubular element 202 is configured to mainly permit aerosols to pass through. Even more preferably configured according to the previously described invention.

The housing 204 could be made of any suitably material or combinations thereof such as, metal, plastic, glass or ceramics The housing 204 comprises a sampling membrane 205 for collecting the non-volatile drug substances from the exhaled breath. The exhaled breath exits the housing through at least one outlet 206. The portable system is sealed after being used and sent to a laboratory 207 to be analyzed. Analysis of the amount of illicit drugs could be performed using a range of methods but preferably methods are Surface enhanced Raman spectroscopy (SERS) or mass-spectroscopy, for example Liquid-chromatography mass-spectroscopy (LCMS).

Alternatively and/or additionally, in some embodiments the portable sampling system is made to be a disposable product. When designed to be a disposable product the housing as well as the mouthpiece is preferably made of a plastic material.

The sampling system and elements for collecting drug substances should be kept clean and preferable be aseptic but could also be used sterile.

Alternatively and/or additionally, in some embodiments of the invention a volume measure unit 208 may be used for detecting the amount of exhaled breath from the tested subject. Preferably the volume measure unit 208 comprising a port arranged downstream the mouthpiece section and upstream the sampling membrane 205. Preferably the port is attached to the tubular element. A pre-defined fraction or portion of the exhaled breath will be extracted through the port and used for calculating the amount of exhaled breath passed through the sampling membrane 205. Preferably the volume measure unit 208 is further comprising a gas volume collecting element, preferably a bag, in communication with the port. The gas volume collecting element has a predefined volume when expanded. The volume of exhaled breath through passed through the sampling membrane 205 may be proportional to the volume of the bag when full.

Alternatively to a gas volume collecting element, such as a bag, a flow meter could be used with an indicator, such as indicators changing colour, may be used to indicate when a pre-determined volume has passed through the sampling membrane.

In FIG. 3 is an embodiment of a portable sampling system 30 is depicted comprising a housing 301, with a sampling membrane 302, a tubular element 303 with a mouthpiece section 308 and a selective trap section, and a volume measure unit comprising a port 307 and a gas volume collecting element 304. The volume measure unit is used for calculating the volume of exhaled breath passing through the sampling membrane 302.

The sampling membrane could be placed anywhere in the housing 301. Preferably the sampling membrane is fastened to the inner walls of the housing 301. The housing 301 is preferably constructed out of two or more parts, a first part with an inlet 305 and one part with at least one outlet 306.

The mouthpiece section 308 and tubular element 303 is detachable and in fluid communication with the housing 301 via the inlet 305. The tubular element 303 is acting as a pre-filter for filtering out saliva and/or mucus and/or large particles and/or aggregates from the exhaled breath, according to what has previously been described. Thus a cleaner sampling membrane, such as a filter membrane, to be analyzed is obtained which may result in better and more accurate analysis. Other advantages with using a tubular element 303 is the prevention of contamination between subjects and sample Alternatively and/or additionally, in some embodiments the mouthpiece section 308 and tubular element 303 is not detachable but integrated with the first part of the housing 301.

Connected either to the tubular element 303 or between the mouthpiece section 308 and the inlet 305 is a port 307 for extracting a portion or fraction of the exhaled breath from the subject. The extracted exhaled breath is used to blow up a gas volume measuring element 304, such as non-elastic bag or an elastic balloon. In this embodiment a non-elastic bag made of plastic is used since it requires less force to be blown up and will automatically stop when full.

When the bag is full the exhaled breath passing through the sampling membrane can be calculated since it will be proportional to volume of the bag. For example, by extracting a tenth of the volume exhaled by the subject, a full two liter bag means that 18 liter has passed through the sampling membrane (20 liter exhaled in total).

Additionally, in some embodiments the port may comprise a one-way valve so that the extracted breath will only enter the bag but not leave.

Alternatively and/or additionally, in some embodiments the port utilizes the back pressure created by the sampling membrane to extract the exhaled breathe through the port 307.

Alternatively, in some embodiments, a flow meter could be used with an indicator, such as indicators changing colour, may be used to indicate when a pre-determined volume has passed through the sampling membrane.

The extracted portion or fraction of the exhaled breath being measured is proportional to the predefined volume of exhaled breath passing through the sampling membrane. Thus by measuring this fraction or portion and by knowing the ratio of air being extracted and air passing through the sampling membrane the total amount of exhaled breath passing through the sampling membrane may be determined.

The exhaled breathe will, after flowing through the tubular element 303, travel into the housing 301 and be brought into contact with the sampling membrane, preferably a filter membrane.

The drug substances being non-volatile compounds conveyed by aerosols in the exhaled breath is collected by the sampling membrane, such as preferably a filter membrane, as the exhaled breath is permeated through the sampling membrane.

It should be noted that the sampling membrane 302 which being a filter membrane is not to be confused with an electronic or chemical sampling units and/or traps. The sampling element 302 is a physical entity on which the drug substance is collected. Collection may in different embodiments be based on various principles, singly or in combination, comprising depositing, catching, fastening, condensing of non-volatile constituents on the sampling element 302.

Using a filter membrane allows for a low pressure drop through the portable system 30 making it easy and comfortable to exhale through it. This is important since many drug addicts experience problems with their lungs.

Figure 3:
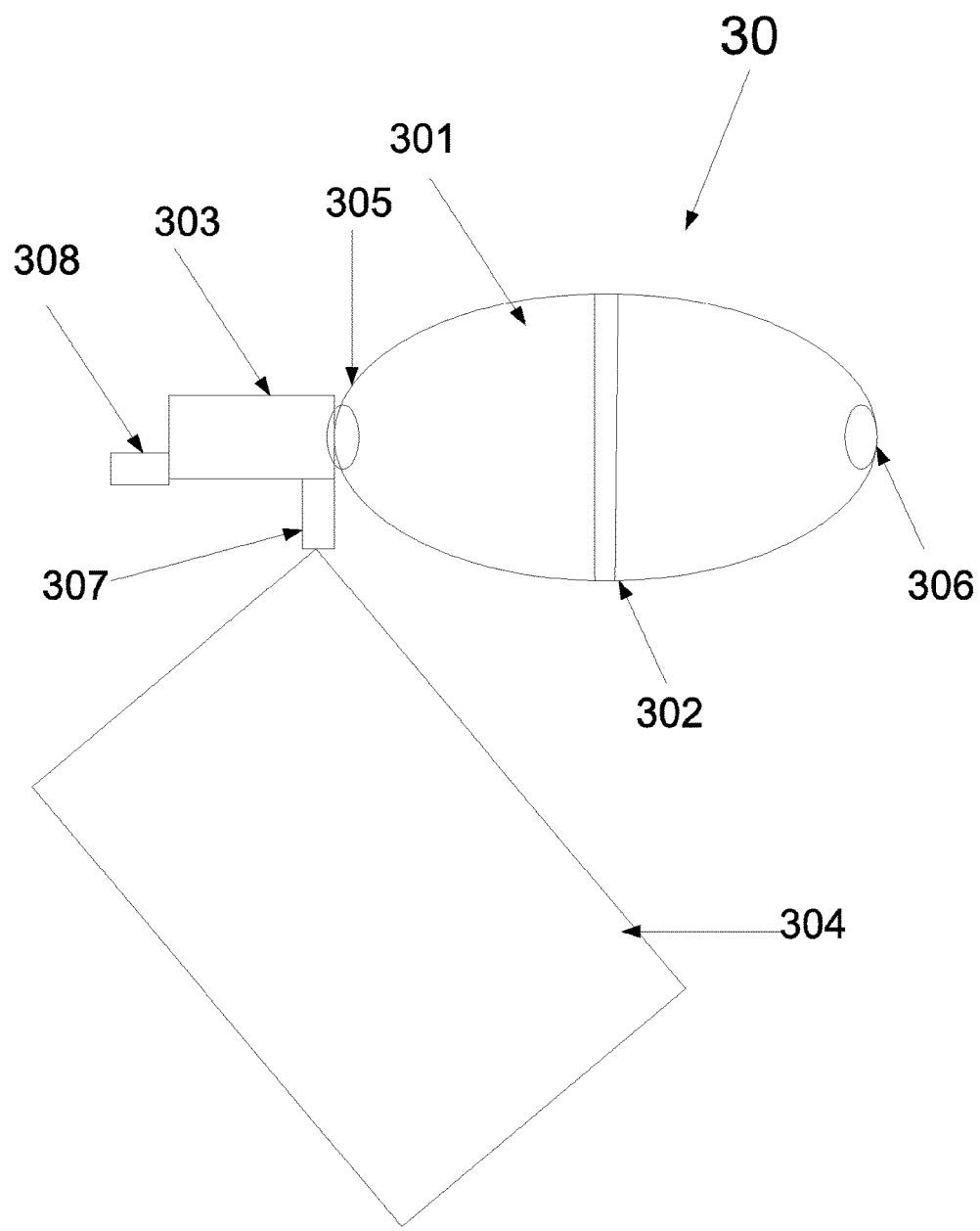
FIG. 3 is an embodiment of a portable sampling device showing a housing with a sampling element being a filter membrane.

In the embodiment depicted in FIG. 3, the filter membrane is placed to block the path for the exhaled breath through the portable system 30. In other embodiments the filter could be placed along the side of any of the walls of the housing 301.

There are many possibilities for fastening the filter membrane is needed, either by using a separate support structure retaining the filter, which may be an element that is either fastened to the inside walls of the housing 301 or a segment being slide onto a first part of the housing during the assembly before the second part of the housing is mounted.

Alternatively and/or additionally, in some embodiments the filter membrane is fastened direct onto the inside walls of the housing 301, either by glue or by heat and thereby melting a small part of the edge of the filter membrane.

The second part of the housing is either screwed or slid onto the first part of the housing. The second part comprises at least one outlet 306. Alternatively and/or additionally, in some embodiment the housing 301 comprises at least two outlets 306. This will aid to avoid a subject being tested to block the outlet and thereby blowing up the measuring element 304 with minimum exhaled breath being permeated through the filter membrane In an embodiment of the portable device 30 the sampling element 302 is a filter membrane made of synthetic and/or half-synthetic fibers for the exhaled breath to diffuse through.

The filter membrane will have a structure that catches the aerosols and thereby collects the drug substances being exhaled while letting gas pass through. The aerosol particles comprise the non-volatile drug compounds. Preferably the filter membrane is operable to collect the aerosols from the air with a high volumetric capacity while maintaining a low pressure drop across the filter substrate.

Alternatively and/or additionally, in some embodiments the filter membrane may be an electrostatic filter made of fibers.

Alternatively and/or additionally, in some embodiments the filter membrane may be of a non-woven polymeric fibrous that may be an electret.

Alternatively and/or additionally, in some embodiments the filter membrane is an electrostatic filter being preferably a non-woven filter membrane comprising a blend of acrylic fibers and polypropylene fibers. The filter membrane could have a density (sometimes called grade or weight) in the range 23 up to 500 g/m2. But it has been shown that the range 130 up to 300 g/m2 is preferred. Even more preferably is the range 200 up to 280 g/m2.

Alternatively and/or additionally, in some embodiments the non-woven layer could be attached to at least further layer. Further layers could be used to enhance a filter membrane's physical properties or improve filtration performance. The extra layer could be a carrier, preferably a polypropylene spunbonded carrier. The spunbond carrier may have a scrim weight in the range 10 up to 20 g/m2, preferably 15 g/m2.

For example a three layered filter membrane comprising one non-woven layer with a density of 250 g/m2 and two layers being carriers each with a scrim weight of 15 g/m2 will have a air flow resistance of about 36 Pa at 9.5 m/min media velocity.

Alternatively and/or additionally, in some embodiments, the filter membrane may be corrugated to enhance the filtering area within a given housing volume.

The portable system is configured and adapted to have a sensitive for illicit drugs high enough to obtain results of a standard that could be used as proof in court. Other advantages are that the test may be performed anywhere at a low cost and short lead time before obtaining a result. Since no specially trained personnel are needed and the test is does not need to be performed at, for example, a hospital.

Other advantages are that the invented portable sampling system is neither invasive, e.g. Blood sampling, nor intruding on personal integrity, e.g. urine sampling. Even known issues with methods used today, related to samples and specimens taken from a subject to be tested are avoided. For instance for blood samples, and especially for urine samples are a risk of the subject exchanging the samples or using clean samples from another subject to avoid being discovered with traces of illicit drugs. The suspected subject can also be tested immediately and does not need to be transported to have the test done later. Hence a more accurate result of the level of an illicit drug at the time of for example an arrest can be obtained.

In FIG. 4A-C one embodiment of the invention is illustrated at different stages. FIG. 4A depicts a tubular element 40 before being assembled and mounted. 401 shows the mouthpiece section with an inlet, 402 shows the selective trap section of the tubular element, 403 shows the outlet, 404 the port for extracting a portion of the exhaled breath and 405 shows the baffles used to obtain the non-straight gas flow path.

FIG. 4B illustrates the device 41 when being ready to be used: 401 shows the mouthpiece section; 402 the tubular section comprising the baffles; 407 is the inlet to the housing 406; 408 shows the outlet from the housing 406; 404 is the port for extracting a portion of the exhaled breath for determining the volume of exhaled breath passing the sampling membrane. The illustration does not show the volume measure unit (i.e. the bag) attached to the extraction port 404.

FIG. 4C is illustrating a used sampling device 42. The mouthpiece section and tubular element is detached and plugs 409, 410 are mounted to the inlet 407 and the outlet 408 of the housing 406. This will seal off the housing 406 and the sampling membrane comprised inside. At this stage the portable sampling device 42 is ready to be sent to a laboratory, for example by post. In FIG. 4C it is shown that the housing 406 is made of two parts 411 and 412 mounted together The process of manufacturing a portable device according to the embodiments described herewithin when the housing is made in plastic could be formed the following way (reference to the parts shown in FIG. 4A-C): a first part, for example, 412 of a housing is heated and thereby enlarging the circumference of the first part 412. When seating a filter membrane in close proximity to the large opening being approximately the middle of the device, at least one compound in the filter membrane will melt at the edge of the filter membrane. This will stick or fastening the filter membrane to the inner wall of the first part 412. The first part of the housing 412 could then be slid or screwed or snapped onto the second part 411. Thus a tight fit may be obtained when the first part 412 cools off and its circumference decreases.

Figure 5:
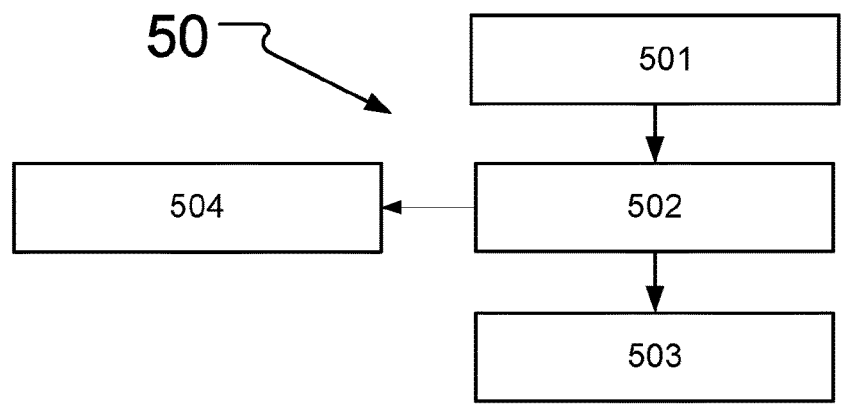
FIG. 5 is showing a flow-chart illustrating a method for using a portable device configured to collect a sample from exhaled breath of a subject.

FIG. 5 is a flow-chart illustrating a method 50 for using a portable system configured to collecting a sample 502 from exhaled breath from a subject. Briefly, FIG. 5 illustrates detecting the presence and/or determining the quantitative amount 503 of at least one illicit drug substance or compound in a collected sample. The illicit drug compounds will be collected as aerosols, being non-volatile particles and/or compounds, from the exhaled breath. The method comprising of: A subject exhaling 501 into the invented portable system; a sampling unit will collect a sample 502 comprises drug substances or compounds; the collected sample will be extracted from the sampling membrane and analyzed 503 using mass-spectroscopy or SERS.

With reference to FIG. 5, a subject will exhale 501 in and out; preferably the subject will exhale into the portable system until a specific volume of exhaled breath has been passed through the sampling membrane, such as preferably a filter membrane.

Alternatively and/or additionally, in some embodiments the subject has to exhale either for a certain time or for a fixed number of times such as 1 to 10 times into a portable system. When breathing a fixed number of times each exhale could be set to last for a fixed time.

To measure a specific volume, one preferred method is to use a port between either located on the mouthpiece or between the mouthpiece and the inlet of the housing. A portion of the exhaled breath will be extracted 504 through the port and blow up an element such as a non-elastic bag. Hence when the bag is full, the volume of said bag will be proportional to the volume passed through the sampling membrane.

Alternatively and/or additionally, in some embodiments a bag with elastic properties can be used.

A deep breath is preferred to reach exhaled breath from deep lying lung portions such as the central or the peripheral lung regions.

The exhaled breath will then be collected 502 by the sampling element, i.e. an easy to breathe through filter membrane, suitably for collecting drug substances before it exits the system. The filter membrane is preferably made of synthetics and/or half synthetics fibers; preferably the filter membrane has electrostatic-properties. Using a filter membrane will create a small, light weighted and easy to use method that can be used everywhere by anyone to detect if a subject is under influence of an illicit drug. The sampling method is of such high quality that the obtained results are of a court approved standard. These results are obtain using a method that is neither invasive, e.g. Blood sampling, nor intruding on personal integrity, e.g. urine sampling. Hence the known drawbacks with these methods are prevented.

After being used, the housing of the sampling system will sealed off by sealing the inlet and the outlet and be sent to a laboratory, whereby the collected compounds in the filter are removed and analyzed 503 using an appropriate analyzing method such as mass-spectroscopy or SERS.

Figure 6:
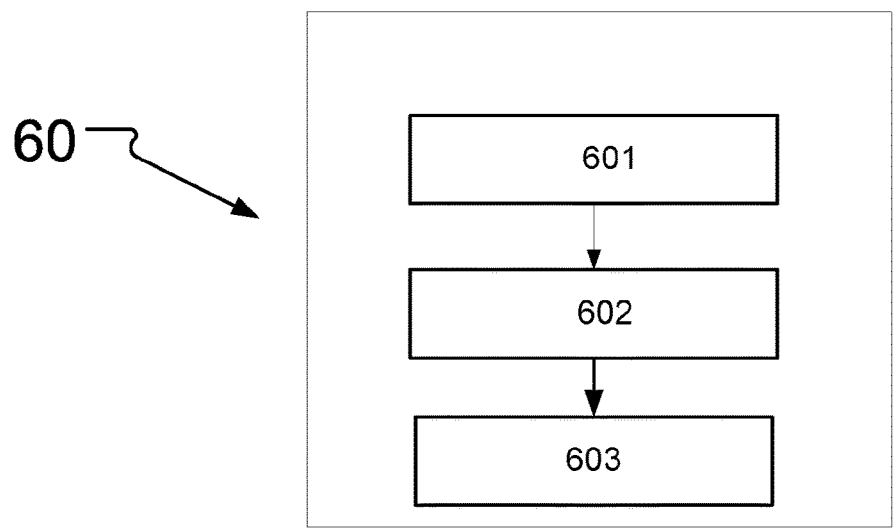
FIG. 6 illustrates a system for detecting the presence or determining the quantitative amount of at least one drug compound in exhaled breath.

FIG. 6 illustrates a system 60 for detecting the presence or determining the quantitative amount of at least one drug compound in exhaled breath. The system comprising a portable drug testing device 602 for handheldly collecting a sample from exhaled breathe from a subject 601. The device 602 could be according to any embodiment described herein. Further, the system 60 comprises a sensor unit 603 for analyzing the collected compounds in the testing device 602. The sensor could be any know type of sensor but preferably mass spectroscopy or SERS. To be able to analyze the collected sample the content of the filter membrane in the device 602 is extracted. This could be done for example by using a solvent to be analyzed using the sensor unit 603. Another method is heating the filter and thereby evaporating the content of the filter for example onto a SERS surface.

In the following further examples of implementations of the invention and how an analysis may be performed is demonstrated. These original observations demonstrate drug testing based on sampling of expired air.

Example 1

Sampling of Drugs of Abuse from Exhaled Human Breath Using Filter Membrane

Table 1 shows sampling of methadone from exhaled breath using a filter membrane comprising one layer being a non-woven electrostatic filter with a blend of acrylic fibers and polypropylene fibers with a density of 250 g/m2 and two carriers each with a scrim weight of 15 g/m2. The tests where performed at 4 different occasions. The first column shows the diameter of the used filter, the second the sampling time the third the amount of methadone collected per minute the fourth the obtained range of methadone among the tested subjects and the fifth column the number of subjects tested.

TABLE 1

| Diameter of filter mm | Sampling time min | Methadone pg/min mean ± SD | Range | n |
| --- | --- | --- | --- | --- |
| 47 | 3 | 86 ± 52 | 18-168 | 6 |
| 32 | 3 | 112 ± 89 | 47-266 | 5 |
| 32 | 3 | 92 ± 62 | 28-199 | 6 |
| 32 | 1 | 204 ± 116 | 21-326 | 6 |

Table 2 shows sampling of methadone in breath from a pre-study when using variable densities of the electrostatic filter membrane. Type is the density of the non-woven layer at each test, the other headlines are the same as for table 1.

TABLE 2

| Type (g/m2) | Methadone pg/min mean ± SD | Range | n |
| --- | --- | --- | --- |
| 150 | 74.4 ± 80.4 | 24-216 | 5 |
| 250 | 71.0 ± 90.1 | 19-231 | 5 |
| 300 | 91.8 ± 110 | 20-287 | 5 |

Table 3 shows sampling of methadone in exhaled breath using two different thicknesses of the electrostatic filter membrane inserted in a sampling device. The subject exhales through the tubular section comprising baffles to trapping large particles and saliva. The tables show that the aerosols will not be trapped by the baffles in the tubular element.

TABLE 3

| Filter thickness | Constructed sampler Methadone pg/min mean ± SD | Range | n |
| --- | --- | --- | --- |
| 1 | 40 ± 27 | 12-85 | 5 |
| 2 | 42 ± 28 | 17-90 | 5 |

Biomarkers

Additionally and/or alternatively, some embodiments of the invention, provides for a portable sampling device for collecting aerosols comprising biomarkers from exhaled breath of a subject for further sensor based analysis. By sampling biomarkers from exhaled breath the device may help providing vital information for early detection and/or diagnosis of diseases or illnesses as well as monitoring of disease progression and/or therapy response.

Devices, systems and methods for sampling non-volatile biomarkers are in accordance with the devices, systems and methods for sampling of drug substances and/or compounds herein described.

Some known non-volatile biomarker that may be transported by aerosols in exhaled breath is comprised in the list comprising lipids, peptides, nucleotides, prostanoids, proteins, DNA or RNA.

These biomarkers may be used for diagnosis of diseases or illnesses, such as cancer (such as lung cancer), asthma, inflammation, infection (such as tuberculosis) and/or oxidative stress or other medical conditions.

In conjunction with the hereinabove described embodiments for sampling drug substances or compounds, which being equally suitable to be used as a portable sampling device for collecting aerosols comprising biomarkers from exhaled breath of a subject for further sensor based analysis, some preferred aspects of the invention provides for a portable sampling device for collecting aerosols comprising biomarkers from exhaled breath of a subject for further sensor based analysis. The portable sampling device comprising a housing comprising at least one inlet and at least one outlet for the exhaled breath to exit through, and a sampling membrane arranged in the housing. The sampling membrane is arranged to collect the aerosols from said exhaled breath.

Additionally, some embodiments further comprising a tubular element having a mouthpiece section for the subject to exhale into, and a selective trap section in fluid communication with the mouthpiece and the inlet of the housing. The selective trap section has a non-straight gas flow path for letting primarily aerosols pass through said tubular element.

Additionally, some embodiments, further comprising a volume measure unit for determining that a pre-defined volume of said exhaled breath has passed through said sampling membrane.

Additionally, some embodiments, wherein said tubular element is detachable from said housing or wherein said tubular element is an integrated part of the housing.

Additionally and/or alternatively, in some embodiments the volume measure unit is configured to measure a volume proportional to the pre-defined volume of the exhaled breath.

Additionally and/or alternatively, in some embodiments a port is arranged downstream the mouthpiece and upstream the sampling membrane and wherein the port is adapted to extract a defined portion of the exhaled breath into the volume measure unit.

Additionally and/or alternatively, in some embodiments, the volume measure unit comprising a gas volume collecting element, such as a bag, having a volume and wherein a port is arranged downstream the mouthpiece and upstream the sampling membrane and wherein the port is adapted to extract a defined portion of the exhaled breath into the volume measure unit. The volume of said gas volume collecting element is proportional to the pre-defined volume of the exhaled breath.

Additionally and/or alternatively, in some embodiments the volume collecting element is a non-elastic bag with a predetermined volume.

Additionally and/or alternatively, in some embodiments the sampling membrane is a filter membrane, preferably an electrostatic filter membrane.

The device according to the invention provides for method to sample aerosols comprise non-volatile biomarkers in exhaled breath. The aerosols comprise non-volatile compounds of at least one biomarker in the exhaled breath and wherein the biomarker is comprised in the list comprising lipids, peptides, nucleotides, prostanoids, proteins, DNA or RNA.

A further aspect of the invention is a use of the device, for non-invasive sampling of exhaled breath detection of biomarkers which may be used for diagnosis of diseases or illnesses, such as cancer, inflammation, infection and/or oxidative stress.

A yet further aspect provides for a method of diagnosis a medical condition of a subject, comprising collecting a sample from exhaled breath of a subject, such as by using the disclosed device, for sensor based analysis of the sample. The method comprising the step of having the subject exhaling into said device; collecting aerosols from the exhaled breath in a sampling membrane of the device; sealing the device off; extracting a content from the sampling membrane; and employing a sensor unit, such as off-site or on-site, for detecting traces of biomarkers in the content, and diagnosing said subject based on a result obtained from the sensor unit.

Additionally, some embodiments of this aspect further comprising measuring a pre-defined fraction of the exhaled breath volume for determining a specific total volume of the exhaled breath passing through the sampling membrane. When the specific total volume is determined as having passed through the sampling membrane terminating the exhalation.

The present invention has been described above with reference to specific embodiments. However, other alternatively and/or additionally embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A portable drug sampling device for handheldly collecting a sample from exhaled breath of a subject for further sensor-based analysis, comprising:
a housing comprising at least one inlet and at least one outlet for said exhaled breath to exit through, and a permeable sampling membrane arranged in said housing transversal to a flow of exhaled breath passing through said sampling membrane; and
a tubular element having a mouthpiece section for said subject to exhale into,
wherein said sampling membrane is arranged to collect aerosols from said exhaled breath passing through said sampling membrane;
wherein said tubular element has a selective trap section in fluid communication with said mouthpiece and said inlet of said housing, said selective trap section having a non-straight gas flow path for letting aerosols pass through;
wherein said sampling membrane is a filter membrane; and
wherein said filter membrane comprises at least one layer of non-woven filtration media with a specific weight in the range of 23 g/m3 to 500 g/m3.

2. The device according to claim 1, further comprising a volume measure unit configured to measure a volume proportional to a pre-defined volume of said exhaled breath that has passed through said sampling membrane.

3. The device according to claim 2, wherein a port is arranged downstream said mouthpiece and upstream said sampling membrane and wherein said port is adapted to extract a defined portion of said exhaled breath into said volume measure unit.

4. The device according to claim 1, further comprising a volume measure unit comprising a gas volume collecting element having a volume and wherein
a port is arranged downstream said mouthpiece and upstream said sampling membrane and wherein said port is adapted to extract a defined portion of said exhaled breath into said volume measure unit; and
wherein said volume of said gas volume collecting element is proportional to said defined volume of said exhaled breath.

5. The device according to claim 4, wherein said volume collecting element is a non-elastic bag with a predetermined volume.

6. The device according to claim 1, wherein said filter membrane comprises at least one further layer being a spunbonded carrier with a scrim weight of 10 to 20 g/m$^3$.

7. The device according to claim 1, wherein said filter membrane has a filter surface to be passed by exhaled gas of approximately 800 mm$^2$ and a pressure drop of 36 Pa at 9.5 m/min media velocity.

8. The device according to claim 1, wherein said filter membrane is made of a blend of acrylic fibers and polypropylene fibers.

9. The device according to claim 1, wherein said tubular element further comprises:
an inlet, and an outlet in connection with a lumen;
at least two baffles, each having a height of at least a length of a radius of the lumen;
and wherein said baffles are arranged on different sides of the lumen to deny an exhaled breath a straight path through said lumen of said tubular element, thereby creating said selective trap section, which primarily said aerosols in said exhaled breath are permitted to pass through.

10. The device according to claim 9, wherein each baffle comprises orifices with a size that only permits said aerosols to pass through.

11. The device according to claim 1, wherein said aerosols comprise non-volatile compounds of at least one drug substance in said exhaled breath.

12. The device according to claim 11, wherein said drug substance comprises one or more of: an amphetamine, MDMA, *cannabis*, a cannabinoid, an opiate, 6-AM, cocaine, a benzodiazepine, propoxyphene, methadone, buprenorphine, tramadol, LSD, cathinone, GHB, meprobamate, Z-drugs, tryptamine, and an anabolic steroid.

13. The device according to claim 1, further comprising in combination a sensor unit for analyzing a sample collected from exhaled breath of a subject by means of said device, the combination forming a system for detecting the presence or determining the quantitative amount of at least one drug compound in said exhaled breath.

14. The device according to claim 1, wherein said filter membrane further comprises an electrostatic filter membrane.

15. The device according to claim 1, wherein said housing and tubular element are removably connected for separation after use with an outlet of said tubular element communicating with the inlet of the housing.

16. A method of screening a person for drugs, comprising:
collecting a sample from exhaled breath of a subject for analysis of said sample, said collecting comprising said subject exhaling into a device, collecting aerosols from said exhaled breath by passing said exhaled breath through a sampling membrane of said device, wherein said sampling membrane comprises at least one layer of non-woven fabric and is arranged transversal to a flow of exhaled breath through the device;
extracting material comprising said sample from said sampling membrane; and
analyzing said sample for a presence of said drugs.

17. The method according to claim 16, further comprising:
providing a portable drug substance sampling device for collecting said sample from exhaled breath of a subject, said portable sampling device comprising a housing including at least one inlet and at least one outlet for said exhaled breath to exit through with said sampling membrane arranged in said housing between said at least one inlet and at least one outlet to collect aerosols from said exhaled breath, a tubular element having a mouthpiece section for said subject to exhale into in fluid communication with said inlet of said housing;
removing the tubular element from said device after collecting the sample; and
sealing the inlet of the housing after removing the tubular element and sealing the outlet of the housing.

18. The method according to claim 17, wherein:
the tubular element of the device includes a port arranged between said mouthpiece section and the inlet of the housing; and
said collecting further comprises attaching a volume measuring unit to said port and determining that a predefined volume of exhaled breath has passed through the sampling membrane before cessation of collecting.

19. The method according to claim 18, wherein said extracting comprises extracting material from the at least one layer of non-woven fabric using a solvent.

20. The method according to claim 19, wherein said analyzing comprises employing a sensor unit for detecting traces of said drugs in said sample.

21. The method according to claim 20, wherein said sensor unit employs Liquid Chromatography-Mass Spectrometry (LCMS) analysis.

22. The method according to claim 16, further comprising measuring a pre-defined fraction of said exhaled breath volume for determining a specific total volume of said exhaled breath passing through said sampling membrane, said pre-defined fraction of said exhaled breath volume having a volume smaller than the total volume of said exhaled breath passing through said sampling membrane, and when said specific total volume is determined as having passed through said sampling membrane terminating said exhalation and sealing off said device.

23. A portable drug sampling device for handedly collecting a sample from exhaled breath of a subject for further sensor: based analysis, comprising:
a housing comprising at least one inlet and at least one outlet for said exhaled breath to exit through, and a sampling membrane comprising at least one layer of non-woven fabric arranged in said housing transversal to a flow of exhaled breath passing through said sampling membrane;
a tubular element having a mouthpiece section for said subject to exhale into,
wherein said sampling membrane including said at least one layer of non-woven fabric is arranged to collect aerosols from said exhaled breath passing through said sampling membrane; and
wherein said tubular element has a port positioned downstream from said mouthpiece section and upstream from said sampling membrane, and said port is configured to permit attachment of a volume measure unit for determining that a pre-defined volume of said exhaled breath has passed through said sampling membrane.

24. The device according to claim 23, wherein said tubular element includes a selective trap section in fluid communication with said mouthpiece and said inlet of said housing, said selective trap section having a non-straight gas flow path for letting aerosols pass through.

25. The device according to claim 23, wherein the tubular element is removably connectable with the housing, said tubular element having an outlet in communication with the housing inlet when connected thereto such that the tubular element may be connected to receive exhaled breath into the device and removed after exhalation into the device.

26. The device according to claim 25, further comprising plugs configured and dimensioned to seal the housing inlet and outlet after use and removal of the tubular element.

27. The device according to claim 26, wherein said at least one layer of non-woven fabric comprises a blend of acrylic fibers and polypropylene fibers adapted to collect said aerosols comprising non-volatile compounds of at least one drug substance in said exhaled breath and has a filter surface to be passed by exhaled gas of approximately 800 mm2 and a pressure drop of 36 Pa at 9.5 m/min media velocity.

28. The device according to claim 25, further comprising plugs configured and dimensioned to seal the housing inlet and outlet after use and separation from the tubular element.

29. The device according to claim 23, further comprising said volume measure unit.

30. The device according to claim 29, wherein said port is adapted to extract a portion of said exhaled breath into said volume measure unit.

31. A portable drug sampling device for handheldly collecting a sample from exhaled breath of a subject for further sensor-based analysis, comprising:
a housing comprising at least one inlet and at least one outlet for said exhaled breath to exit through, and a permeable sampling membrane arranged in said housing transversal to a flow of exhaled breath passing through said sampling membrane; and
a tubular element having a mouthpiece section for said subject to exhale into, wherein said sampling membrane is arranged to collect aerosols from said exhaled breath passing through said sampling membrane;

wherein said tubular element has a selective trap section in fluid communication with said mouthpiece and said inlet of said housing, said selective trap section having a non-straight gas flow path for letting aerosols pass through; and wherein the sampling membrane comprises at least one layer of non-woven fabric attached to the walls of the housing;

the housing comprises at least two connectable parts, a first part including said mouthpiece section and a second part including said outlet; and the selective trap section has baffles to provide said non-straight flow path.

* * * * *